(12) United States Patent
Weiss et al.

(10) Patent No.: US 10,702,699 B2
(45) Date of Patent: Jul. 7, 2020

(54) METHOD AND SYSTEM FOR CARDIAC PACING AND DEFIBRILLATION

(71) Applicant: PROROGO LTD., Tel-Aviv (IL)

(72) Inventors: Abraham Teddy Weiss, Jerusalem (IL); Shimon Rozenheck, Jerusalem (IL); Shraga Gorni, Jerusalem (IL); Mendel Mandelbaum, Jerusalem (IL)

(73) Assignee: PROROGO LTD., Tel Aviv (IL)

( * ) Notice: Subject to any disclaimer, the term of this patent is extended or adjusted under 35 U.S.C. 154(b) by 338 days.

(21) Appl. No.: 15/292,206

(22) Filed: Oct. 13, 2016

(65) Prior Publication Data
US 2018/0104497 A1    Apr. 19, 2018

(51) Int. Cl.
*A61N 1/365* (2006.01)
*A61N 1/39* (2006.01)
*A61N 1/362* (2006.01)

(52) U.S. Cl.
CPC ....... *A61N 1/36507* (2013.01); *A61N 1/3625* (2013.01); *A61N 1/3904* (2017.08); *A61N 1/3987* (2013.01); *A61N 1/3993* (2013.01)

(58) Field of Classification Search
CPC ............................ A61N 1/3625; A61N 1/3987
See application file for complete search history.

(56) References Cited

U.S. PATENT DOCUMENTS

| | | | |
|---|---|---|---|
| 3,566,876 A | 3/1971 | Stoft et al. | |
| 3,798,542 A * | 3/1974 | Dempsey | A61N 1/3937 324/111 |
| 5,078,134 A * | 1/1992 | Heilman | A61B 5/6831 600/508 |
| 5,251,624 A * | 10/1993 | Bocek | A61N 1/3956 607/6 |
| 6,148,233 A | 11/2000 | Owen et al. | |
| 7,865,238 B2 * | 1/2011 | Brink | A61N 1/39 607/7 |
| 2003/0060723 A1 * | 3/2003 | Joo | A61B 5/0535 600/510 |

(Continued)

FOREIGN PATENT DOCUMENTS

| EP | 1 064 963 A1 | 1/2001 |
|---|---|---|
| WO | WO2006/069215 | 6/2006 |

OTHER PUBLICATIONS

International Search Report for PCT Application No. PCT/IL2017/051108 dated Jan. 29, 2018.

(Continued)

*Primary Examiner* — Paula J Stice
(74) *Attorney, Agent, or Firm* — Pearl Cohen Zedek Latzer Baratz LLP

(57) ABSTRACT

A system for cardiac pacing includes circuitry and at least two electrodes, configured to be placed in contact with a chest of a subject. The circuitry is configured to receive electro-cardiogram (ECG) signals from the at least two electrodes, to identify brachycardia or asystole or ventricular tachycardia in the subject based on the received ECG signals, upon identifying brachycardia or asystole or ventricular tachycardia, to shape a mains electrical source signal into a waveform applicable to a transformer for generating a pacing signal, to generate the pacing signal by applying the waveform to the transformer, and to apply the pacing signal through the at least two electrodes to the chest of the subject.

7 Claims, 14 Drawing Sheets

(56) References Cited

U.S. PATENT DOCUMENTS

| | | | |
|---|---|---|---|
| 2004/0172068 A1* | 9/2004 | Sullivan | A61N 1/39 607/5 |
| 2004/0243185 A1* | 12/2004 | Weiss | A61N 1/3906 607/5 |
| 2007/0032830 A1 | 2/2007 | Bowers | |
| 2007/0049974 A1 | 3/2007 | Li et al. | |
| 2008/0177342 A1* | 7/2008 | Snyder | A61N 1/3906 607/8 |

OTHER PUBLICATIONS

Search report for European Patent Application No. EP 17 85 9778, dated Mar. 20, 2020.

* cited by examiner

METHOD AND SYSTEM FOR CARDIAC PACING AND DEFIBRILLATION

FIELD OF THE INVENTION

The present invention relates to cardiac pacing and defibrillation, and more particularly to method and systems for cardiac pacing and defibrillation.

BACKGROUND OF THE INVENTION

Sudden cardiac death caused by arrhythmias such as severe bradycardia, asystole, ventricular tachycardia or fibrillation are a major cause of death among the adult population in developed countries. Sudden cardiac death accounts for 1,000 cases per day in the U.S. alone, most of them occurring at home or at the office.

Ventricular tachycardia is characterized by the onset of a very high heart rate. It may be treated by applying a pacing pulse train to the patient's heart with a frequency above the heart rate of the patient and progressively reducing the frequency to a normal frequency corresponding to 60 to 80 beats per minute.

Bradycardia is characterized by the onset of a very slow heart rate. Bradycardia may lead to asystole, commonly known as a flat line, since no cardiac activity is detectable. Bradycardia, or asystole, may be treated by applying a pacing pulse train to the patient's heart with a frequency corresponding to 60 to 80 beats per minute. Bradycardia and asystole are defined as non-shockable rhythms and are not treatable by standard Automatic External Defibrillators (AED).

Ventricular fibrillation can be halted and normal cardiac activity restored by applying electrical defibrillation, or an electrical high energy shock applied to the patient's heart.

SUMMARY OF THE INVENTION

There is thus provided, in accordance with some embodiments of the present invention, a system for cardiac pacing including circuitry and at least two electrodes, configured to be placed in contact with a chest of a subject. The circuitry is configured to receive electro-cardiogram (ECG) signals from the at least two electrodes, to identify brachycardia or asystole or ventricular tachycardia in the subject based on the received ECG signals, upon identifying brachycardia or asystole or ventricular tachycardia, to shape a mains electrical source signal into a waveform applicable to a transformer for generating a pacing signal, to generate the pacing signal by applying the waveform to the transformer, and to apply the pacing signal through the at least two electrodes to the chest of the subject.

In accordance with some embodiments of the present invention, the circuitry includes a pacing circuit source and wave-shaping unit configured to be synchronized to the mains electrical source signal using a zero crossing detector.

There is further provided, in accordance with some embodiments of the present invention, a system for cardiac pacing and defibrillation including circuitry and at least two electrodes, configured to be placed in contact with a chest of a subject. The circuitry is configured to receive electro-cardiogram (ECG) signals from the at least two electrodes, to identify a cardiac arrhythmia in the subject based on the received ECG signals; if the identified cardiac arrhythmia is bradycardia or asystole or ventricular tachycardia, to shape a mains electrical source signal into a first waveform applicable to a transformer for generating pacing signals, to generate the pacing signals by applying the first waveform to the transformer, and to apply the pacing signals through the at least two electrodes to the chest of the subject; and if the identified cardiac arrhythmia is ventricular fibrillation, to shape the mains electrical source signal into a second waveform applicable to the transformer for generating defibrillation signals, to pre-magnetize a transformer core of the transformer, to generate the defibrillation signals by applying the second waveform to the pre-magnetized transformer, and to apply the defibrillation signals through the at least two electrodes to the chest of the subject.

In accordance with some embodiments of the present invention, the circuitry is configured to shape the mains electrical source signal into the second waveform for generating the defibrillation signal by using a high frequency signal generator.

In accordance with some embodiments of the present invention, the circuitry is configured to pre-magnetize the transformer core by applying a series of current pulses in a current waveform generated from the mains electrical power source signal to a primary coil of the transformer.

In accordance with some embodiments of the present invention, the circuitry is configured to apply the series of current pulses to the primary coil when a secondary coil of the transformer is coupled to a dummy resistive load.

In accordance with some embodiments of the present invention, the circuitry includes a communication unit configured to call emergency medical services.

In accordance with some embodiments of the present invention, the circuitry includes an audio instruction and alarm unit configured to audibly guide a user of the system.

In accordance with some embodiments of the present invention, the circuitry includes a pacing circuit source and wave-shaping unit configured to be synchronized to the mains electrical source signal using a zero crossing detector.

There is further provided, in accordance with some embodiments of the present invention, a method for cardiac pacing and defibrillation, including in circuitry, receiving electro-cardiogram (ECG) signals from at least two electrodes configured to be placed in contact with a chest of a subject. A cardiac arrhythmia is identified in the subject based on the received ECG signals. If the identified cardiac arrhythmia is bradycardia or asystole or ventricular tachycardia, a mains electrical source signal is shaped into a first waveform applicable to a transformer for generating pacing signals. The pacing signals are generated by applying the first waveform to the transformer. The pacing signals are applied through the at least two electrodes to the chest of the subject. If the identified cardiac arrhythmia is ventricular fibrillation, the mains electrical source signal is shaped into a second waveform applicable to the transformer for generating defibrillation signals. A transformer core of the transformer is pre-magnetized. The defibrillation signals are generated by applying the second waveform to the pre-magnetized transformer. The defibrillation signals are applied through the at least two electrodes to the chest of the subject.

BRIEF DESCRIPTION OF THE DRAWINGS

In order for the present invention, to be better understood and for its practical applications to be appreciated, the following Figures are provided and referenced hereafter. It should be noted that the Figures are given as examples only and in no way limit the scope of the invention. Like components are denoted by like reference numerals.

DETAILED DESCRIPTION OF THE INVENTION

Figure 1:
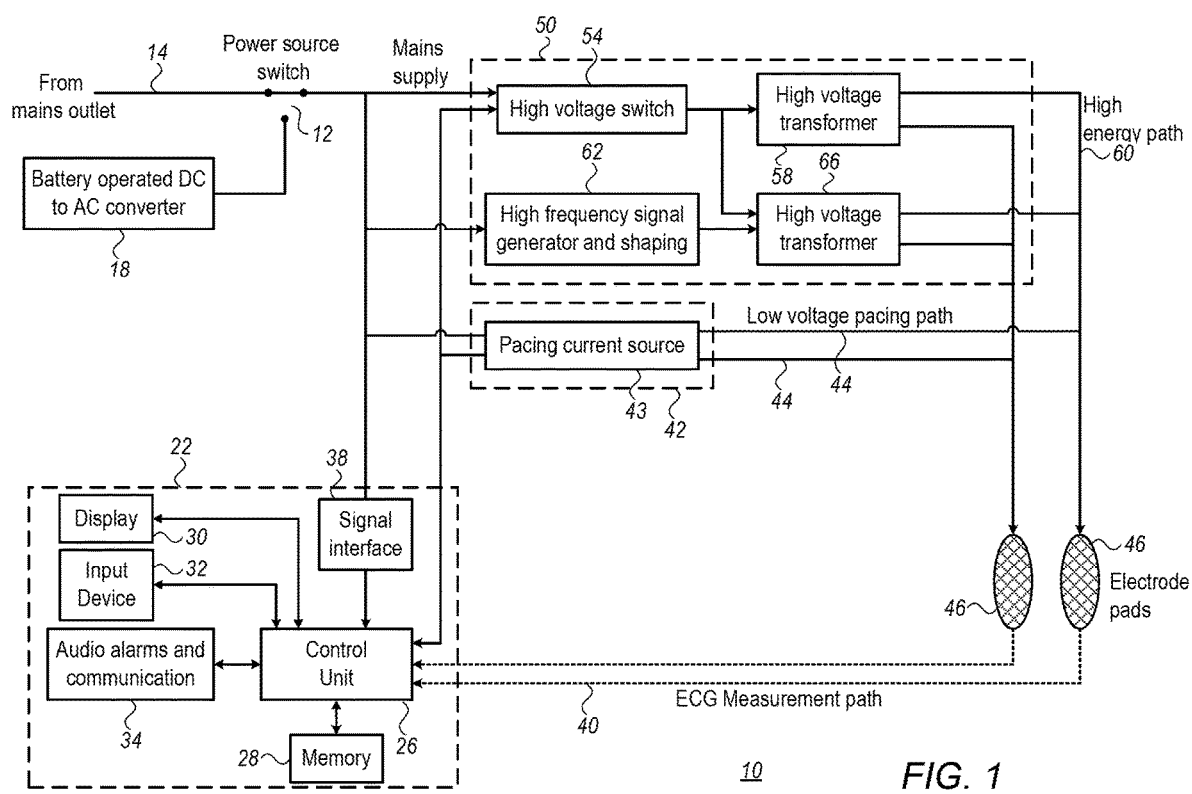
FIG. 1 is a functional block diagram schematically illustrating a pacing and defibrillation system, in accordance with some embodiments of the present invention.

In the following detailed description, numerous specific details are set forth in order to provide a thorough understanding of the invention. However, it will be understood by those of ordinary skill in the art that the invention may be practiced without these specific details. In other instances, well-known methods, procedures, components, modules, units and/or circuits have not been described in detail so as not to obscure the invention.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium (e.g., a memory) that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method embodiments described herein are not constrained to a particular order or sequence. Additionally, some of the described method embodiments or elements thereof can occur or be performed simultaneously, at the same point in time, or concurrently. Unless otherwise indicated, use of the conjunction "or" as used herein is to be understood as inclusive (any or all of the stated options).

When a subject experiences the onset of life threatening cardiac arrhythmias such as bradycardia, asystole, ventricular tachycardia, and/or fibrillation, administering immediate treatment to the patient for mitigating these problems is critical to the subject's survival. When ventricular fibrillation occurs in a work office or in public places (e.g., airport, stadium), installed standard automatic external defibrillators (AED) may be used to administer a high voltage defibrillation shock to the patient to halt fibrillation and restore the patient's heart beat to a normal rhythm. AEDs may shorten the intervention delay until medical assistance arrives to assist the subject or patient.

The standard AED generates a high voltage defibrillation pulse by charging a high voltage capacitor from a battery and discharging the capacitor through the defibrillation electrodes contacting the patient's chest. The pulse may then propagate through the patient's chest to his heart. The high voltage pulse waveform from the discharging capacitor may include a characteristic exponentially decreasing voltage. However, some cardiac arrhythmias in the subject are not alleviated by defibrillation pulses delivered to the chest of the subject. For example, pacing signals applied to the subject may be used to alleviate bradycardia, or asystole, or ventricular tachycardia. However, standard AEDs do not provide pacing capabilities due to energy limitations which must be applied to the patient for long periods of time quickly draining the battery supply.

Some embodiments of the present invention described herein provide a pacing and defibrillation system for identifying cardiac arrhythmias in the chest of a subject by electrical signals generated by the heart (e.g., electro-cardiogram) and delivering external pacing and/or defibrillation signals to the subject suitable for treating the identified cardiac arrhythmia. At least two electrodes connected to the portable defibrillator and pacing system may be used for receiving electro-cardiogram signals and to externally apply the pacing and/or defibrillation signals to the body of the subject, typically to the chest of the subject. In various embodiments, the pacing and defibrillation system may be portable, or the pacing and defibrillation system may be in a fixed position, such as mounted on a wall, for example, connected to a mains electrical power supply.

In some embodiments, adhesive pads may be used and may be held in contact with the skin of the subject by use of an adhesive. The adhesive pads may be connected to the portable pacing and defibrillation system. In some embodiments, solid and/or wet gel adhesive electrodes may be used.

In the absence of trained health care professional, the system may continue to monitor the cardiac arrhythmia and may deliver life-saving pacing and/or defibrillation signals to the patient until the cardiac arrhythmia may be mitigated or until trained medical professionals may arrive to assist the subject.

In some embodiments of the present invention, the portable defibrillator and pacing system may include circuitry powered by a mains electricity supply and/or powered from a separate DC power supply and input to a DC-to-AC converter. It may be deployed, for example, at home or at an office, wherever a mains electrical supply, such as a wall outlet is available. The portable defibrillator and pacing system may remain connected to the mains electrical supply to be ready to apply pacing and/or defibrillation signals as needed to a subject who may be experiencing the sudden onset of cardiac arrhythmias, for example. A continuous connection of the portable pacing and defibrillator system to the mains electrical supply may permit administering pacing signals to the subject over long periods of time without the need to recharge a battery.

In some embodiments of the present invention, the pacing and/or defibrillation signals applied to the subject's chest may be generated in the circuitry by shaping the mains electrical supply signal and applying the shaped signal through a transformer to achieve higher energy levels.

The mains electrical source, or supply, as referred to herein may include a general-purpose alternating-current (AC) electric power supply. Mains electric power source may be referred to as household power, household electricity, office electricity house current, powerline, domestic power, wall power, line power, AC power, city power, street power, and/or grid power or any suitable power supply that may be used to power the circuitry. In some embodiments, the mains electrical source may generate a 110/220 V signal at 50/60 Hz depending on the country where the portable defibrillator and pacing system may be deployed, for example.

FIG. 1 is a functional block diagram schematically illustrating a pacing and defibrillation system 10, in accordance with some embodiments of the present invention. System 10 may be connected via a switch 12 to a mains electrical power source 14, or alternatively to a battery operated DC-to-AC converter 18, connected to an external battery, such as a car battery, for example. Mains electrical power source 14 may include an AC mains outlet. Switch 12 may include, for example, a manual switch or an automatic voltage sensing switch. DC-to-AC converter 18 may be used, for example, when the mains electrical power source 14 is not available and an external battery may be coupled to DC-to-AC converter 18 instead.

System 10 may include a microcomputer unit 22. Microcomputer unit 22 may include a control unit 26, a memory 28, an output device 30, an input device 32, an audio alarm and communication unit 34, and signal interface 38. Audio alarm unit 34 may be used to audibly alert the user of system 10 by providing audible warnings and instructions to the user. Audio alarm and communication unit 34 may include functions for contacting emergency services. Audio alarm and communication unit 34 may include circuitry to automatically telephone or communicate the location and condition of the subject to emergency medical services, for example, by any suitable cellular or wireless protocols. Audio alarm and communication unit 34 may audibly instruct information the user about communicating with the emergency medical services. Signal interface 38 may include additional circuitry for separating low voltage components from high voltage components, such as the circuitry for generating the defibrillation signals, for example, in system 10. Signal interface 38 may also include signal leveling circuitry.

Control unit 26 may include one or more processing units, e.g., of one or more computers and/or microprocessors. Control unit 26 may be configured to operate in accordance with programmed instructions, or software, stored in memory 28. Control unit 26 may be capable of executing an application using electrodes attached to the subject for identifying cardiac arrhythmia in a subject, to assess whether to apply pacing or defibrillation signals to the subject, and to assess progress in alleviating the cardiac arrhythmia of the subject.

Control unit 26 may be implemented, for example, by circuit components bonded to a printed circuit board, by field programmable gate array (FPGA) devices, and/or by a single chip or die capable of performing all the functions described herein.

Control unit 26 may communicate with output device 30. For example, output device 30 may include a computer monitor or screen. Control unit 26 may communicate with a screen of output device 30 to display visual feedback to the user of system 10 as to the progress of the steps performed by system 10 in alleviating the cardiac arrhythmia in the subject. In some embodiments, output device 30 may include a printer, display panel, or another device capable of producing visible or tactile output.

Control unit 26 may communicate with input device 32. For example, input device 32 may include one or more of a keyboard, keypad or pointing device for enabling a user to input data or instructions for operation of control unit 26.

Control unit 26 may communicate with memory 18. Memory 18 may include one or more volatile or nonvolatile memory devices. Memory 18 may be utilized to store, for example, programmed instructions for operation of control unit 26, data or parameters for use by control unit 26 during operation, or results of operation of control unit 26

In operation, control unit 26 may execute a method using electrodes contacting the chest of a subject for identifying cardiac arrhythmia in a subject, to assess whether to apply pacing or defibrillation signals to the subject, and to assess progress in mitigating the cardiac arrhythmia of the subject.

System 10 may include a pacing subsystem 42 which may further include a pacing current source 43. Upon control unit 26 assessing that the cardiac arrhythmia may be alleviated by applying pacing signals, pacing subsystem 42 may generate the pacing signals which are applied to the subject over a low voltage conducting pacing path 44 to a pair of electrode pads 46 contacting the chest of the subject. In some embodiments, a step down transformer may be used on pacing path 44.

System 10 may include an ECG measurement path 40 wherein ECG signals from electrode pads 46 may be received and processed by control unit 22.

System 10 may include a defibrillation subsystem 50. Upon control unit 26 assessing that the cardiac arrhythmia may be alleviated by applying defibrillation signals, defibrillation subsystem 50 may generate the defibrillation signals which are applied to the subject via a pair of electrode pads 46 contacting the chest of the subject.

In some embodiments of the present invention, defibrillation subsystem 50 may include a first method for generating the defibrillation signal applied to the subject by use of direct wave shaping of the mains voltage waveform from mains electrical power source 14 or from battery operated DC-to-AC converter 18. The mains voltage waveform may be shaped in a high voltage switch unit 54 whose output may be applied to a high voltage step up transformer 58. The generated defibrillation signal from high voltage step up transformer 58 may be applied to the subject over a high energy conducting path 60 using two electrode pads 46 contacting the chest of the subject.

In some embodiments of the present invention, the design of defibrillation subsystem 50 may be configured to yield maximum energy from high voltage step up transformer 58 by pre-magnetizing the transformer core of transformer 58. High voltage transformer 58 may be configured for minimum weight and size.

In some embodiments of the present invention, defibrillation subsystem 50 may include a second method for generating the defibrillation signal applied to the chest of the subject. The mains voltage waveform may be shaped using a high frequency signal generator and shaping unit 62 whose output is applied to a high frequency, high voltage step up transformer 66. The generated defibrillation signal from high frequency, high voltage step up transformer 66 may be applied to the subject over a high energy conducting path 60 using two electrode pads 46 contacting the chest of the subject.

Figure 2:
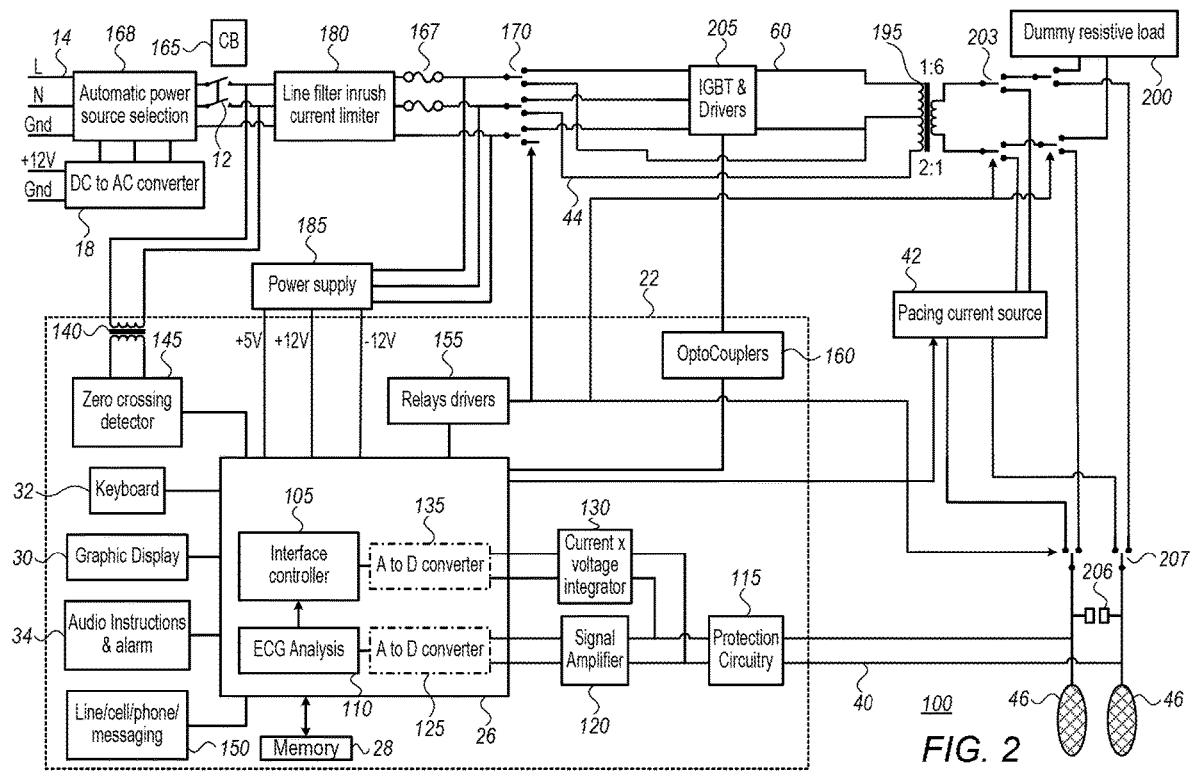
FIG. 2 is a first circuit diagram of a pacing and defibrillation system, in accordance with some embodiments of the present invention.

FIG. 2 is a first circuit diagram 100 of pacing and defibrillation system 10, in accordance with some embodiments of the present invention. System 10 may be connected via switch 12 to mains electrical power source 14, or alternatively to a battery operated DC-to-AC converter 18 when mains electrical power source 14 is not available. An automatic power source selection unit 168 may choose which power source to use and may set the position of switch 12. A circuit breaker (CB) 165 may be used to prevent the leakage of voltage spikes, for example, which may damage the circuitry shown in first circuit diagram 100. The signal from mains electrical power source 14 may be applied via circuit breaker 165 to a Line Filter Inrush Current Limiter 180 which may be used to limit any current spikes into the circuitry. A secondary semiautomatic internal fuse 167 may provide additional protection for the circuitry.

Microcomputer unit 22 may be used to receive electrocardiogram (ECG) signals from electrode pads 46 along ECG measurement path 40. Control unit 26 may include an interface control unit 105, and an ECG analysis unit 110. In some embodiments, control unit 26 may include a first A-to-D converter 125 and a second A-to-D converter 135. In some embodiments, first A-to-D converter 125 and second A-to-D converter 135 may be separate from control unit 26. Interface control unit 105 may be used to initiate the generation of pacing and/or defibrillation signals based on the cardiac arrhythmia identified by ECG analysis unit 110. ECG analysis unit 110 may receive ECG signals from electrodes 46 contacting the chest of the subject. Protection circuitry 115 coupled to electrodes 46 may be used to protect and isolate low voltage microcomputer unit 22 from a leakage of high voltages during defibrillation sequences applied to the chest of the subject using common electrodes 46. The analog ECG signals may be amplified by a signal amplifier and filter unit 120 and coupled to ECG analysis unit 110 via first A-to-D converter 125. Signal amplifier and filter unit 120 may be used to level and filter the received analog ECG signals for first A-to-D converter 125.

ECG analysis unit 110 may relay information to interface controller 105 differentiating as to whether to apply defibrillation signals and/or pacing signals after analysis of the received ECG signals. If pacing signals are selected to be applied to the subject, the starting heart rate may be relayed from ECG analysis unit 110 to interface control unit 105. If defibrillation signals are selected to be applied to the subject, the energy to be delivered to the heart of the subject in the defibrillation signal may be relayed from ECG analysis unit 110 to interface control unit 105, for example. When a defibrillation signal is delivered to the subject using electrode pads 46, the energy delivered in the defibrillation signal may be sampled in a current voltage integrator unit 130 and fed back to the interface control unit 105 via a second analog-to-digital converter 135 for further analyses in assessing the effectiveness of the defibrillation signals in restoring a normal heart rhythm.

Based on the analyses performed by ECG Analysis unit 110 described above, interface control unit 105 may select whether a defibrillation or a pacing signal may be applied to the subject by setting the position of a selection relay 170 via relay drivers 155. The position of selection relay 170 may route the signal from mains electrical power source 14 via secondary semiautomatic internal fuse 167 to circuitry in defibrillation path 60 or pacing path 44. A power supply unit 185 may supply DC power at different voltages to circuitry in microcomputer unit 22 as well as circuitry along defibrillation path 60 and pacing path 44 via selection relay 170. Power supply unit 185 may be powered by mains electrical power source 14, or from a separate power supply such as a battery. Nevertheless, the pacing and/or defibrillation signals are generated from the signal from mains electrical power source 14.

An optocoupler 160 may be used by microcomputer unit 22 to control the high voltage components used in shaping the signal from mains electrical power source 14 according to the command signals from interface controller 105. Optocouplers, or opto-isolators, may be used to prevent high voltages from affecting the system, in this case high voltage leakage into the logic circuitry, for example, of control unit 26.

On defibrillation path 60, the signal from mains electrical power source 14 may be shaped and amplified by an insulated gate bipolar transistor (IGBT) and driver unit 205 and coupled to a first primary coil of a transformer 195 with a turns ratio of 1:6. Similarly, signals along pacing path 44 may also be coupled to second primary winding of transformer 195 with a turns ratio of 2:1, which may be used for lower signal voltages (e.g., 110 V) from mains electrical power source 14. At the secondary side of transformer 195, when a defibrillation signal may be used, a high voltage relay 203 routes the defibrillation signal to electrode pads 46. If a pacing signal is used, high voltage relay 203 routes the signal from the secondary coil of transformer 195 to a pacing circuit source unit 42 while the secondary relay ports in relay 203 are terminated with a dummy resistive load 200.

A second high voltage relay 207 may be used to select between the defibrillation path or the pacing path may be used to route the selected defibrillation and/or pacing signal to electrode pads 46. A high voltage surge protector 206 may be placed between the connections to electrode pads 46 as shown in FIG. 2.

In order to synchronize the waveform shaping of the signal from mains electrical power source 14, the signal from switch 12 may be coupled to a stepdown transformer 140 in microcomputer unit 22 and used to feed the sinusoidal signal from mains electrical power source 14 to a zero crossing detector unit 145. The output of zero crossing detector unit 145 may be coupled to control unit 26 and may be used as a synchronization signal for system 10 to the sinusoidal signal from mains electrical power source 14.

Microcomputer unit 22 may also include input device 32, such as a keyboard, for use by the user of system 10 to setup operating parameters of system 10 such as, for example, emergency phone numbers (landline and cellular), SMS phone numbers, neighbors or family phone numbers (e.g., related to the location that system 10 is deployed). Keyboard 32 may be removable or fixed to system 10.

Microcomputer unit 22 may also include output device 30 such as a graphic display. Graphic display 30 may be used, for example, to display messages for guiding and warning the user of system 10, who may be not trained in emergency medical procedures as well as for a user of system 10 with hearing problems. Graphic display 30 may also be used to display information to the user regarding historical information applied to the subject such as ECG waveforms and/or waveforms of the pacing and/or defibrillation signals applied to the subject, such as pacing and/or defibrillation signal waveforms, before and after system 10 identifies cardiac arrhythmia. These displayed waveforms may be stored in memory 28 and may be useful to the trained medical emergency professionals that may later arrive to assist the subject.

Microcomputer unit 22 may also include audio instruction and alarm unit 34 including speakers (not shown in FIG. 2). Audio instruction and alarm unit 34 may be used to guiding users not trained in emergency medical procedures, for example, with voice instructions as to how to apply electrode pads 46 to the chest of the subject, such as the chest of the subject or patient. Audio instruction and alarm unit 34 may be used to audibly issue a warning to the user clear away, or not to contact the subject during the application of the high voltage defibrillation signal, for example, which may harm the user.

Microcomputer unit 22 may also include a communication unit 150 (e.g., line/cell phone and messaging unit 150) which may be used to provide calling capability to emergency services, neighbors and family members of the subject via any suitable and/or predefined methods of communication, such as land line telephony, cellular telephony, wireless and/or messaging communications, for example. Any personal and contact data of the owner of system 10, the subject, and/or emergency medical services, for example, may be entered using keyboard 32 and/or display 30.

Figure 3:
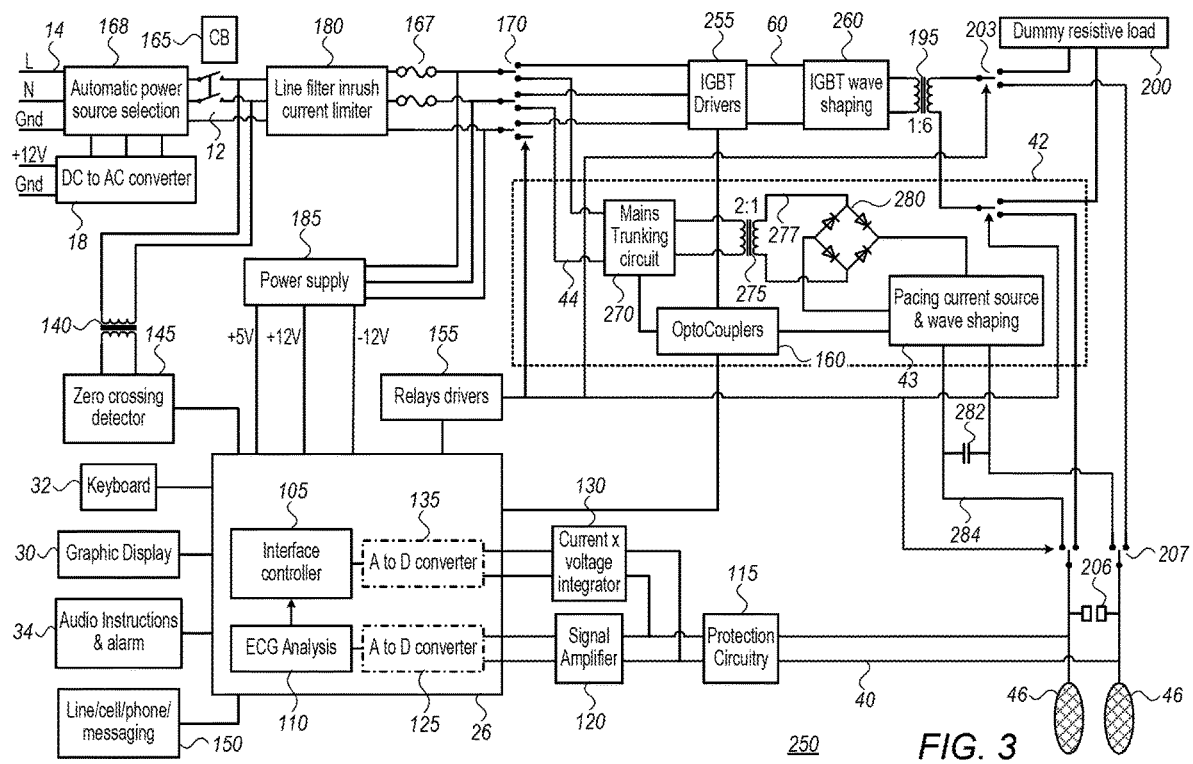
FIG. 3 is a second circuit diagram of a pacing and defibrillation system, in accordance with some embodiments of the present invention.

FIG. 3 is a second circuit diagram 250 of pacing and defibrillation system 10, in accordance with some embodiments of the present invention. Control unit 26 may identify from the ECG analysis that a pacing signal may be applied to the subject. In this case, interface controller 105 may change via relay drivers 155 the position of selection relay 170 such that the signal from mains electrical power source 14 may pass through pacing path 44.

Pacing subsystem 42 may include a mains trunking circuit 270, a step-down transformer 275, a full bridge rectifier 280, and pacing current source and wave shaping unit 43, Pacing signals generated in pacing subsystem 42 applied to the subject may need a variable voltage DC signal up to 150 VDC so as to drive pacing current source 43, a variable current source up to 100 mA. Selection relay 170 may apply the signal from mains electrical power source 14 to the primary winding of transformer 195 shared by both the pacing and defibrillation paths in FIG. 2, or to a separate step down transformer 275 as shown in FIG. 3. In the case where the signal from mains electrical power source 14 may be 110V, 60 Hz, the step down transformer 275 is not needed. Mains trunking circuit 270 may be used as a high power signal chopping circuit controller by control unit 26 for generating pacing signals. Stated differently, mains trunking circuit 270 may generate the pacing waveform by modifying the signal from mains electrical power source 14. Mains trunking circuit 270 may be controlled by interface controller 105 via optocouplers 160. In some embodiments, control unit 26 may change the frequency of the pacing signal to control the cardiac arrhythmia, such as progressively reducing the pacing signal frequency in the case of ventricular tachycardia, for example.

Figure 4A:
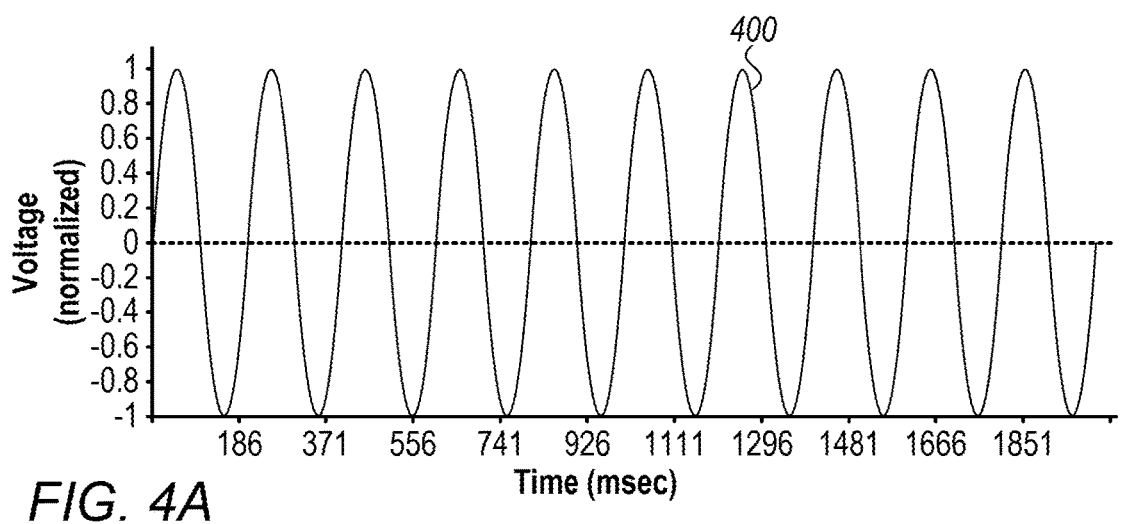
FIG. 4A is a sinusoidal signal from a mains electrical power source, in accordance with some embodiments of the present invention.
Figure 4B:
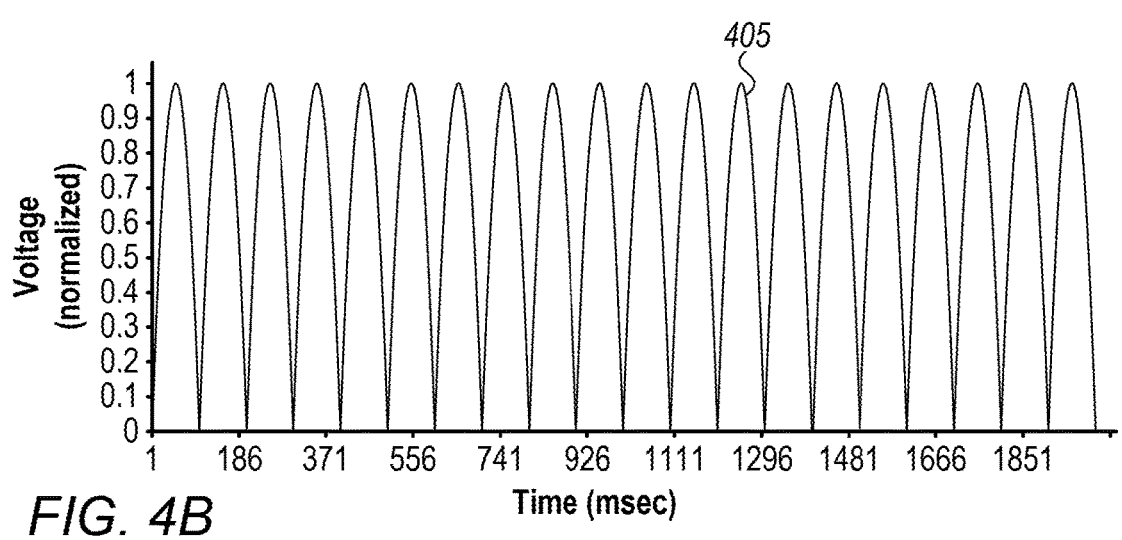
FIG. 4B illustrates a rectified voltage waveform sampled across full bridge rectifier, in accordance with some embodiments of the present invention.
Figure 4C:
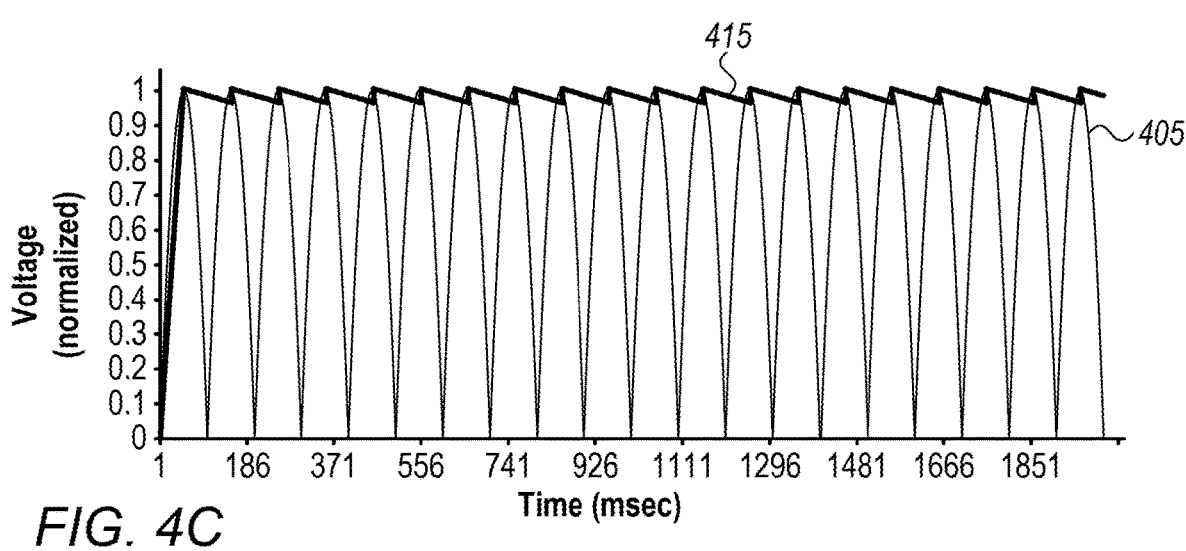
FIG. 4C illustrates a DC signal generated by filtering a rectified voltage waveform, in accordance with some embodiments of the present invention.

FIGS. 4A-4C illustrate signal waveforms sampled at different nodes in second circuit diagram 250, in accordance with some embodiments of the present invention.

FIG. 4A is a sinusoidal signal 400 from mains electrical power source 14, in accordance with some embodiments of the present invention. Voltage waveform 400 may be a 50 Hz voltage signal applied to mains trunking circuit 270, whose output signal may be applied to the primary winding of transformer 275. The output signal 277 at the secondary winding of transformer 275 may be applied to full bridge rectifier 280 as shown in FIG. 3.

FIG. 4B illustrates a rectified voltage waveform 405 sampled across full bridge rectifier 280, in accordance with some embodiments of the present invention. A capacitor 282 is used to filter rectified waveform 405 to generate a DC voltage.

FIG. 4C illustrates a DC signal 415 generated by filtering rectified waveform 405, in accordance with some embodiments of the present invention. The variable DC voltage for the pacing signal may be generated as shown in FIGS. 4A-4C by filtering rectified waveform 405, e.g., DC signal 415.

Figure 5A:
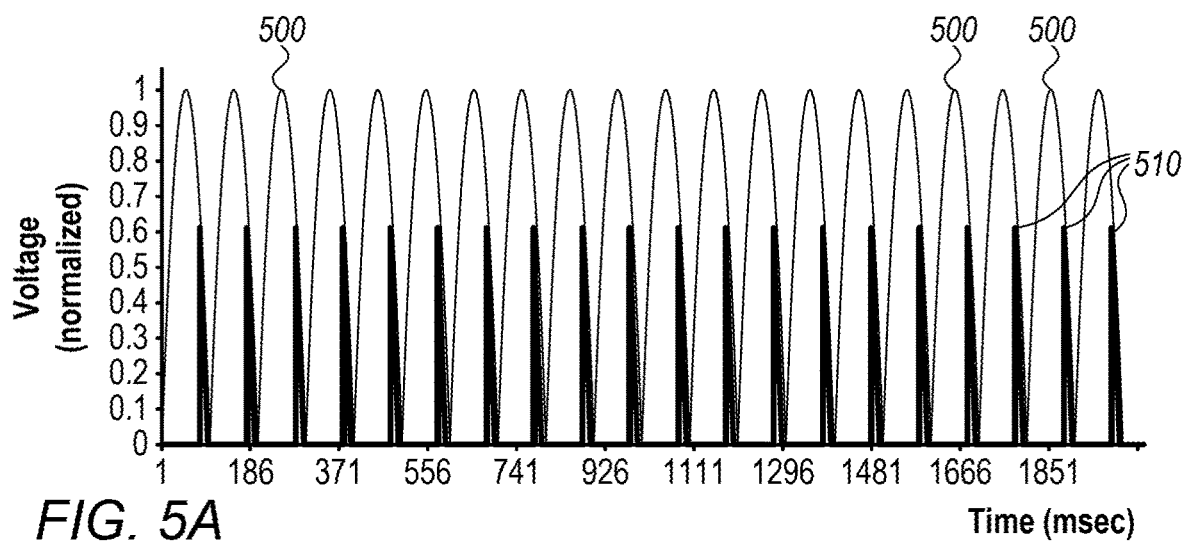
FIG. 5A illustrates a rectified voltage waveform and a truncated waveform, in accordance with some embodiments of the present invention.
Figure 5B:
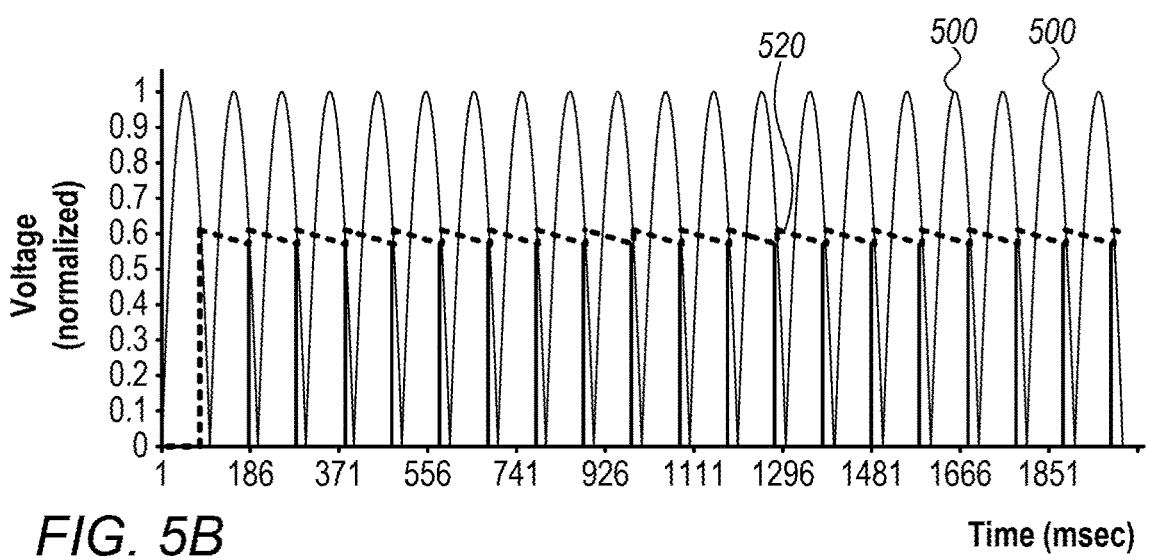
FIG. 5B illustrates a filtered truncated waveform, in accordance with some embodiments of the present invention.
Figure 5C:
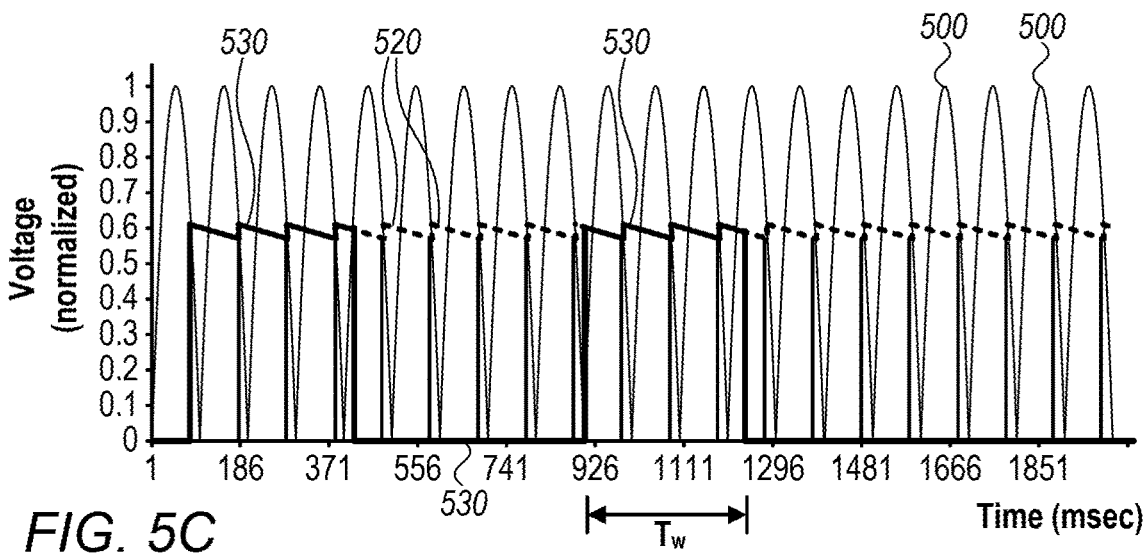
FIG. 5C illustrates a waveform of a pacing signal, in accordance with some embodiments of the present invention.

FIGS. 5A-5C illustrate signal waveforms in generating a pacing signal in pacing subsystem 42, in accordance with some embodiments of the present invention. Pacing Current Source and Wave Shaping Unit 43 may include a pulse width modulation circuit. Pacing Current Source and Wave Shaping Unit 43 may be controlled by interface controller 105 and may be synchronized with the signal from mains electrical power source 14 using zero crossing detector 145.

FIG. 5A illustrates rectified voltage waveform 500 and a truncated waveform 510, in accordance with some embodiments of the present invention. Interface controller 105 may be used to control truncated waveform 510 sampled at a node 284 which is used to generate the variable DC voltage for the pacing signal. Capacitor 282 may filter and reduce the ripple in truncated waveform 510.

FIG. 5B illustrates a filtered truncated waveform 520, in accordance with some embodiments of the present invention. Filtered truncated waveform 520 may include a nearly constant voltage with small ripple. Filtered truncated waveform 520 may be used to generate pacing pulses to be applied to the subject with a duty cycle equivalent to a heart rate of 60 to 180 beats per minute when tachycardia may be detected as the cardiac arrhythmia. Similarly, filtered truncated waveform 520 may be used to generate pacing pulses with a duty cycle equivalent to a heart rate 60 beats per minute (e.g., a normal heart rate) may be applied to the subject when brachycardia or asystole or ventricular tachycardia may be detected as the cardiac arrhythmia.

FIG. 5C illustrates a waveform of pacing signal 530, in accordance with some embodiments of the present invention. Pacing Current Source and Wave Shaping Unit 43 may include a variable current source, which may be controlled by interface controller 105, and may be used to generate a pacing signal 530. Interface controller 105 via relay drivers 155 may position high voltage relay 203 to connect dummy resistive load 200 to the idle high voltage source. Interface controller 105 via relay drivers 155 may also position second high voltage relay 207 so as to couple pacing signal 530 to electrodes pads. In this manner, any residual high voltage may be removed from the pacing signal. Additional protection may be provided by high surge protector 206 which may prevent applying any overvoltage to the subject. The pacing pulse width Tw is shown in FIG. 5C. In some embodiments, the pacing pulse width Tw may be 30-40 msec, for example.

Figure 6:
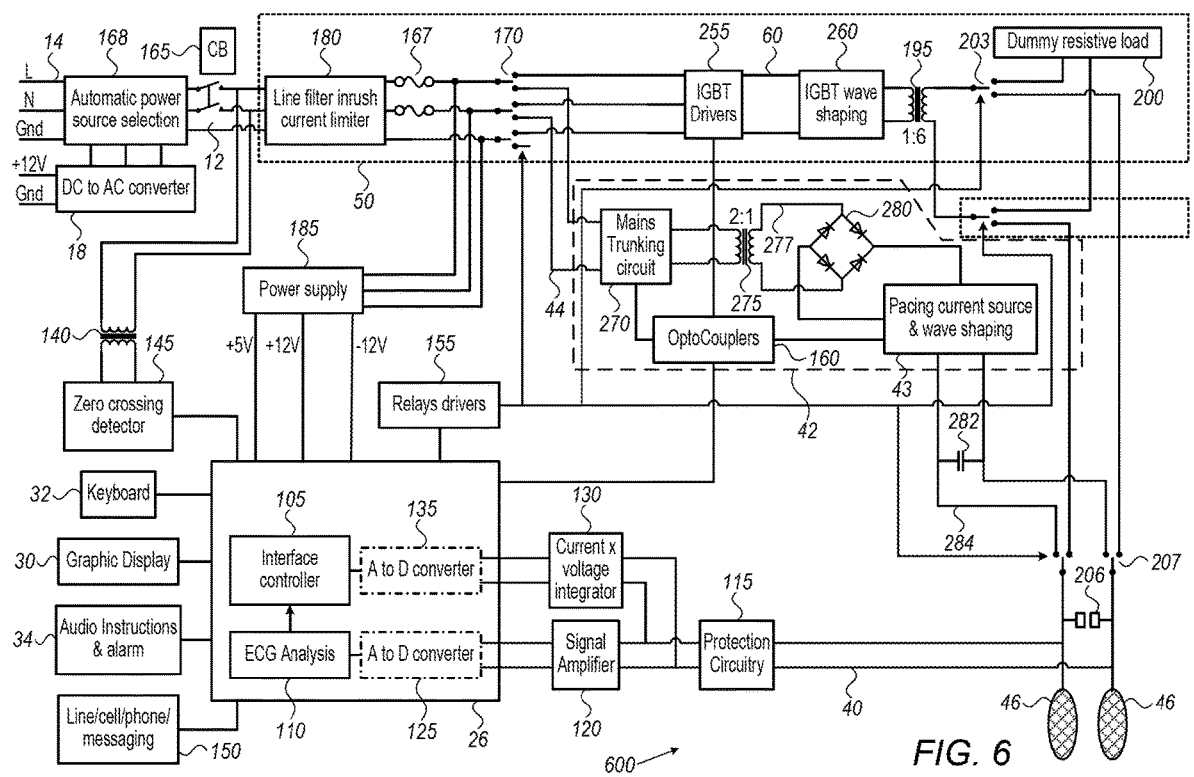
FIG. 6 is a third circuit diagram of a pacing and defibrillation system, in accordance with some embodiments of the present invention.

FIG. 6 is a third circuit diagram 600 of pacing and defibrillation system 10, in accordance with some embodiments of the present invention. Two separate transformers, e.g., transformer 195 and transformer 275 (e.g., 2:1 step-down transformer used in pacing subsystem 42), may be used respectively to generate a defibrillation signal and pacing signal, which may be applied to the subject. When ECG analysis unit 110 determines that defibrillation may be needed to alleviate the identified cardiac arrhythmia, interface controller 105 may set the position of a selection relay 170 via relay drivers 155 to defibrillation path 60 so as to route the signal from mains electrical power source 14 into defibrillation subsystem 50. If mains electrical power source 14 is not available, an external battery may be connected to battery-operated DC to AC converter 18 as a backup.

In some embodiments of the present invention, IGBT drivers 255 are connected to control unit 26 via optocoupler 160 may be used to control high voltage IGBT devices in IGBT wave shaping unit 260. IGBT devices in IGBT wave shaping unit 260 may be turned on and off by IGBT drivers 255 using control signals sent by control unit 26. The control signals from interface controller 105 are based on the analyses performed by ECG Analysis unit 110 on ECG signals received from electrode pads 46.

Interface controller 105 may select a number of defibrillation signal waveforms to be applied to the subject such as a monophasic truncated sine waveform, a biphasic truncated sine waveform, a triphasic truncated sine waveform, and a quadriphasic truncated sine waveform. These waveforms may be generated by turning on and off the high voltage IGBT devices in IGBT wave shaping unit 260.

Figure 7A:
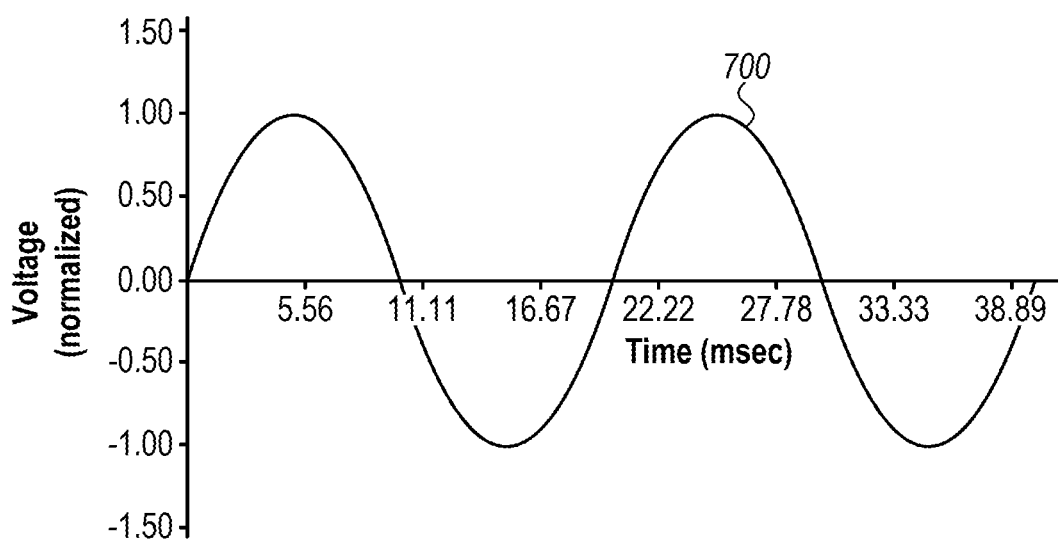
FIG. 7A is a sinusoidal signal from mains electrical power source, in accordance with some embodiments of the present invention.

FIG. 7A is a sinusoidal signal 700 from mains electrical power source 14, in accordance with some embodiments of the present invention.

Figure 7B:
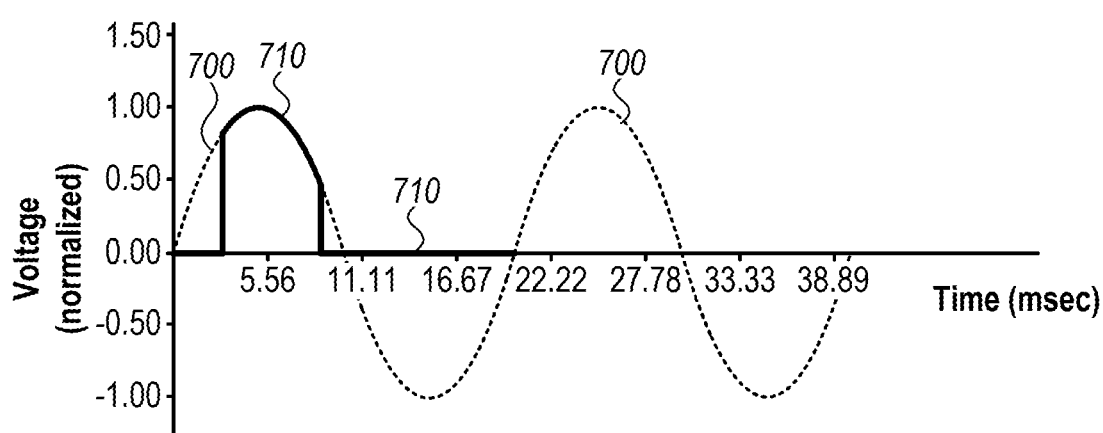
FIG. 7B is a monophasic truncated waveform shaped from a sinusoidal signal from a mains electrical power source, in accordance with some embodiments of the present invention.

FIG. 7B is a monophasic truncated waveform 710 shaped from sinusoidal signal 700 from mains electrical power source 14, in accordance with some embodiments of the present invention.

Figure 7C:
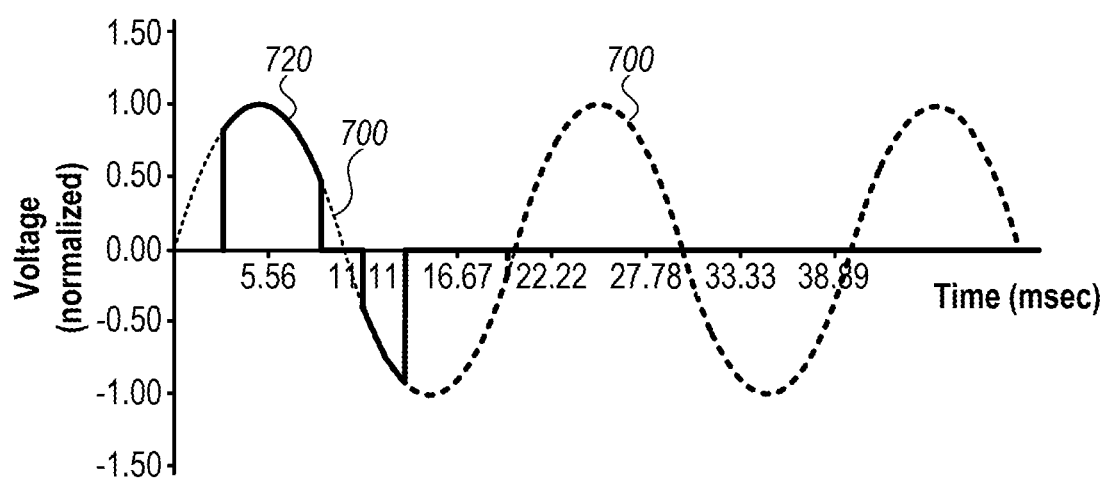
FIG. 7C is a biphasic truncated waveform shaped from a sinusoidal signal from a mains electrical power source, in accordance with some embodiments of the present invention.

FIG. 7C is a biphasic truncated waveform 720 shaped from sinusoidal signal 700 from mains electrical power source 14, in accordance with some embodiments of the present invention.

Figure 7D:
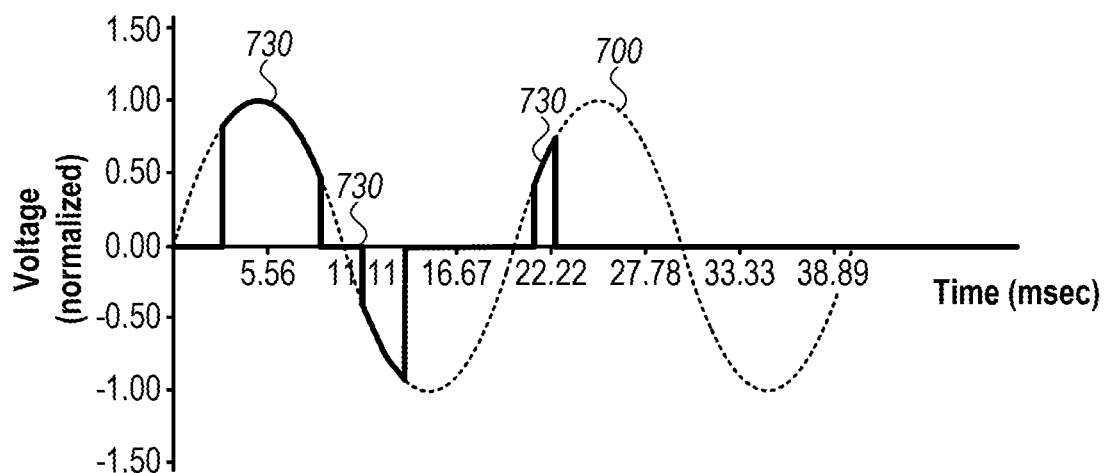
FIG. 7D is a triphasic truncated waveform shaped from a sinusoidal signal from a mains electrical power source, in accordance with some embodiments of the present invention.

FIG. 7D is a triphasic truncated waveform 730 shaped from sinusoidal signal 700 from mains electrical power source 14, in accordance with some embodiments of the present invention.

Figure 7E:
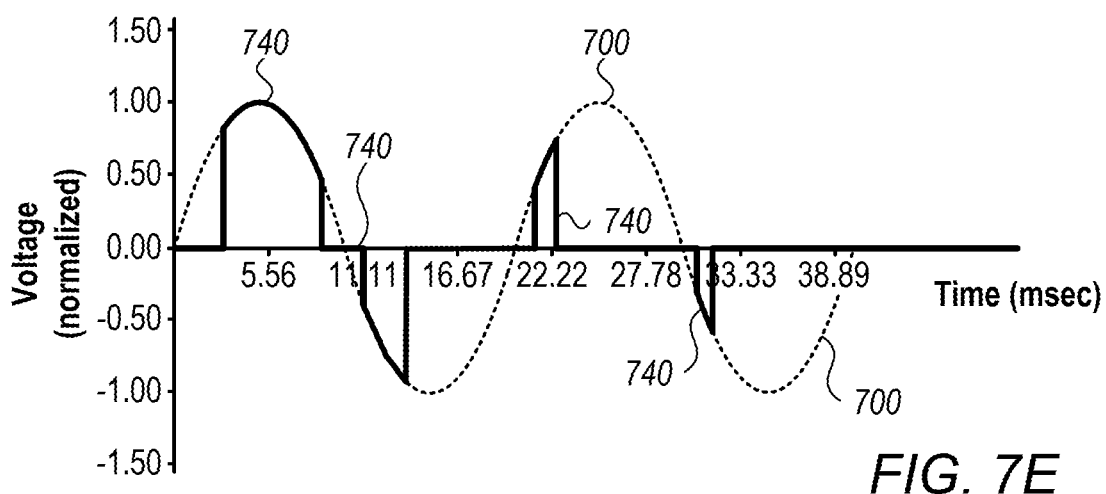
FIG. 7E is a quadriphasic truncated waveform shaped from a sinusoidal signal from a mains electrical power source, in accordance with some embodiments of the present invention.

FIG. 7E is a quadriphasic truncated waveform 740 shaped from sinusoidal signal 700 from mains electrical power source 14, in accordance with some embodiments of the present invention.

Different defibrillation signals corresponding to the waveforms shown in FIGS. 7B-7E may be generated by shaping sinusoidal signal 700 from mains electrical power source 14 in IGBT wave shaping unit 260 controlled by instructions received from interface controller 105, and by applying these shaped waveforms to high voltage step up transformer 195. High voltage relay 203 may use a resistive dummy load 200, to present an impedance to high voltage transformer 195 during the pre-magnetization process in order to maximize energy transfer through the transformer in the defibrillation signal. Resistive dummy load 200 may also be used in the case where a single transformer may be used for pacing as discussed previously.

Second high voltage relay 207 may be used to select between the defibrillation signal generated using step up transformer 203 and the pacing signals generated using step down transformer 275, and routing the selected signal to electrode pads 46. In the case where pacing signals are used, high voltage relay 203 may be switched to dummy resistive load 200 so as to prevent stray voltages from leaking into electrode pads 46. High voltage surge protector 206 may prevent applying any overvoltage to the subject.

Figure 8:
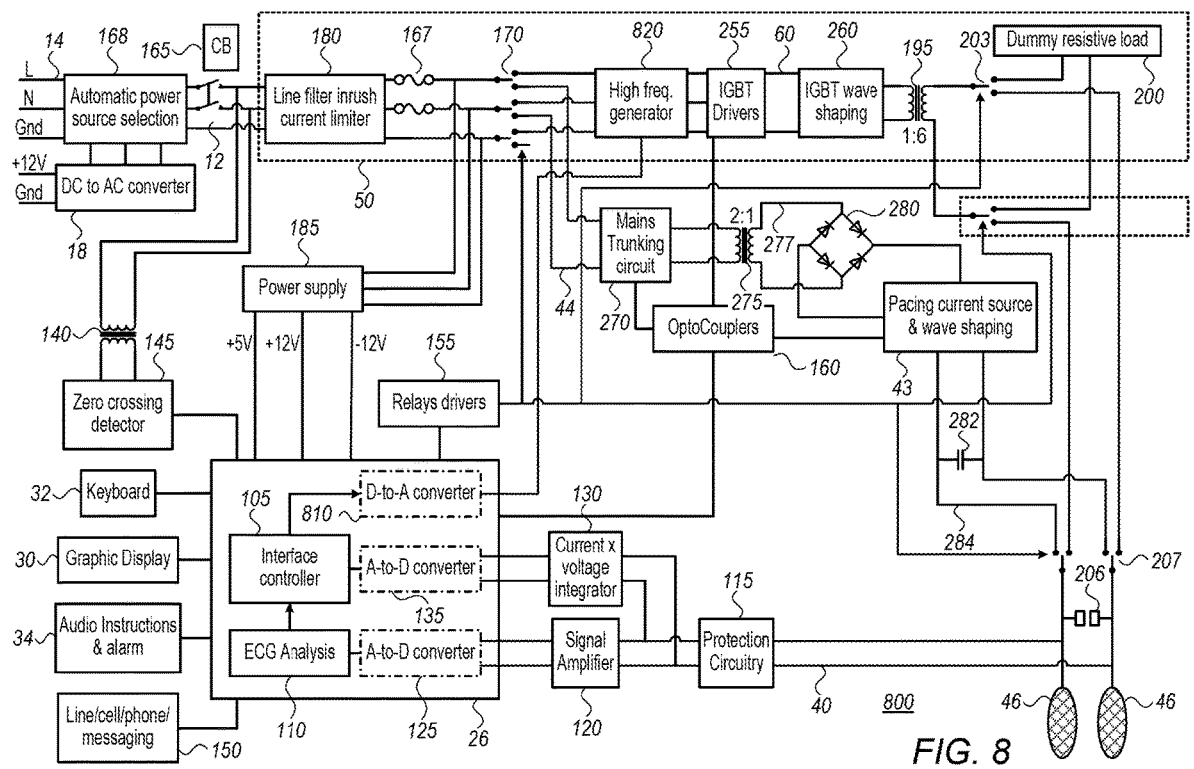
FIG. 8 is a fourth circuit diagram of a pacing and defibrillation system, in accordance with some embodiments of the present invention.

FIG. 8 is a fourth circuit diagram 800 of pacing and defibrillation system 10, in accordance with some embodiments of the present invention. Two separate transformers, e.g., transformer 195 and transformer 275 (e.g., 2:1 step-down transformer used in pacing subsystem 42), may be used respectively to generate a defibrillation signal and pacing signal, which may be applied to the subject. However, defibrillation subsystem 50 may be use a high frequency generator 820 in shaping the signal from mains electrical power source 14, which may be used to generate the defibrillation signal.

The signal from mains electrical power source 14 may be input to high frequency generator 820 to generate a high frequency sinusoidal signal ranging in frequency from several KHz to a few MHz. Interface controller 105 may generate a truncated sine wave via an digital-to-analog converter 810. In some embodiments, digital-to-analog converter 810 may be integrated into interface controller 105. IGBT drivers 60 may be used to control IGBT devices in IGBT wave shaping unit 260. IGBT drivers 60 may be receive control signals from control unit 26 via optocoupler 160. The IGBT devices may be turned on and off by control signals sent by control unit 26 (e.g., interface controller 105) to the IGBT devices in IGBT wave shaping unit 260 so as to generate a defibrillation waveform that is a combination of the high frequency signal from high frequency generator 820 and an envelope signal generated by interface controller 105. The defibrillation signal applied to the subject may be generated by applying the defibrillation waveform to transformer 195.

Figure 9A:
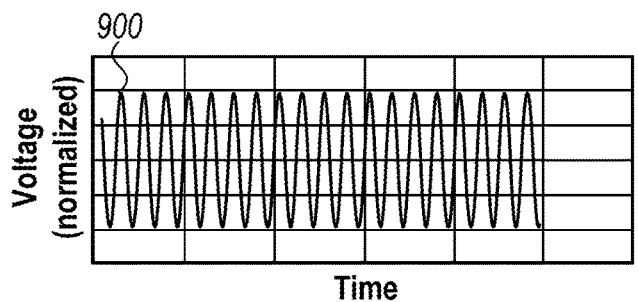
FIG. 9A is a high frequency, high voltage sinusoidal waveform from a high frequency generator, in accordance with some embodiments of the present invention.

FIG. 9A is a high frequency, high voltage sinusoidal waveform 900 from high frequency generator 820, in accordance with some embodiments of the present invention.

Figure 9B:
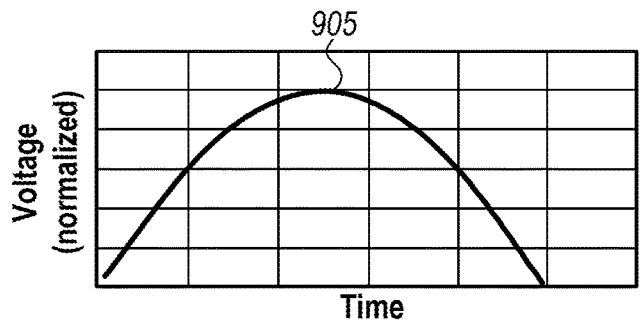
FIG. 9B is a sinusoidal envelope waveform, in accordance some embodiments of the present invention.

FIG. 9B is a sinusoidal envelope waveform 905, in accordance some embodiments of the present invention. Sinusoidal envelope waveform 905 is the signal from mains electrical power source 14.

Figure 9C:
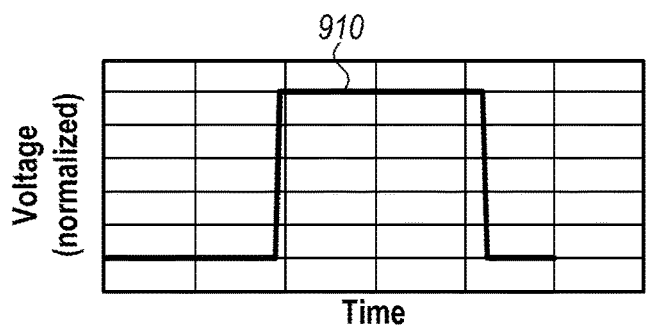
FIG. 9C is an output waveform from a pulse width generator, in accordance with some embodiments of the present invention.

FIG. 9C is an output waveform 910 from a pulse width generator, in accordance with some embodiments of the present invention. Output waveform 910 may be generated from a pulse width generator in microcomputer 22.

Figure 9D:
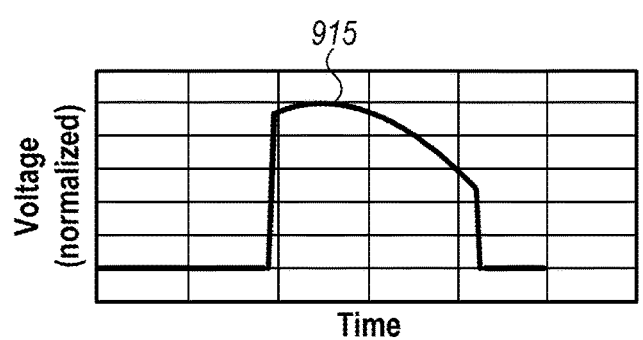
FIG. 9D is a gated envelope waveform, in accordance with some embodiments of the present invention.

FIG. 9D is a gated envelope waveform 915, in accordance with some embodiments of the present invention.

Figure 9E:
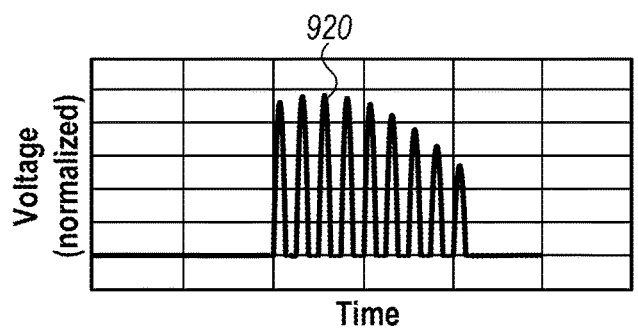
FIG. 9E is a defibrillation waveform, in accordance with some embodiments of the present invention.

FIG. 9E is a defibrillation waveform 920, in accordance with some embodiments of the present invention.

Figure 10A:
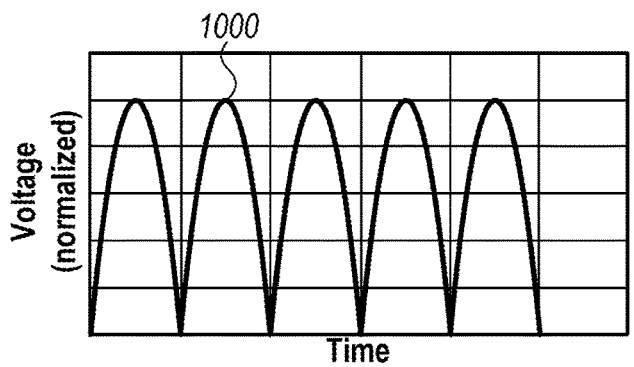
FIG. 10A is a 50 Hz rectified voltage waveform, in accordance with some embodiments of the present invention.

FIG. 10A is a 50 Hz rectified voltage waveform 1000, in accordance with some embodiments of the present invention.

Figure 10B:
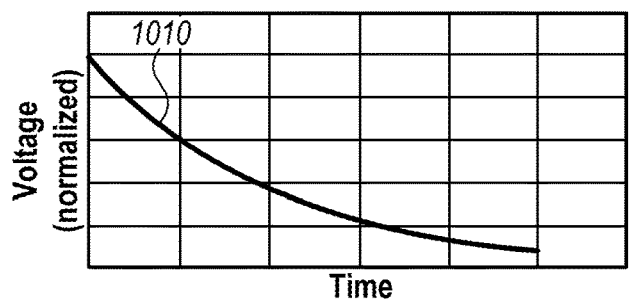
FIG. 10B is a high voltage capacitor discharge waveform, in accordance some embodiments of the present invention.

FIG. 10B is a high voltage capacitor discharge waveform 1010, in accordance some embodiments of the present invention. In some embodiments, the defibrillation signal applied to the patient may be generated in the circuitry shown the previous circuit diagrams (e.g., in FIGS. 6 and 8) to be similar to defibrillation signals generated in existing standard AEDs.

Figure 10C:
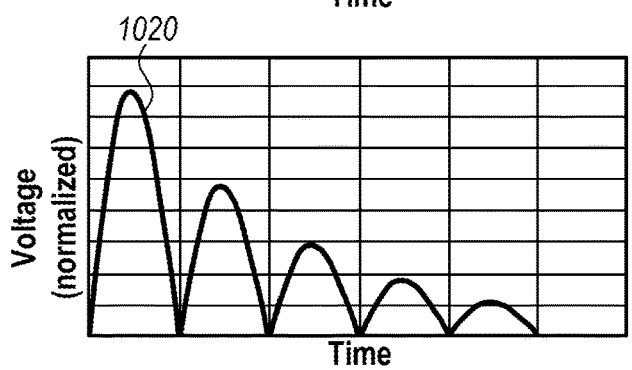
FIG. 10C is a modified 50 Hz rectified voltage waveform, in accordance with some embodiments of the present invention.

FIG. 10C is a modified 50 Hz rectified voltage waveform 1020, in accordance with some embodiments of the present invention.

Figure 10D:
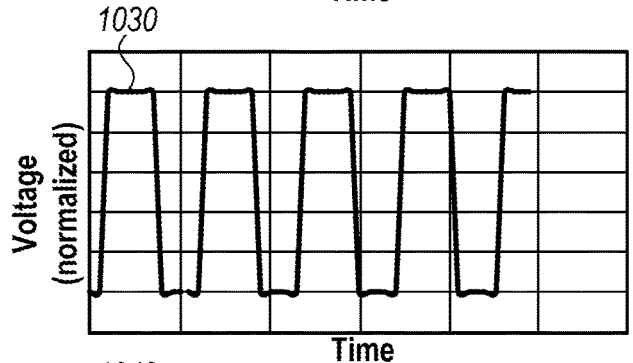
FIG. 10D is a pulse width generator output waveform, in accordance with some embodiments of the present invention.

FIG. 10D is a pulse width generator output waveform 1030, in accordance with some embodiments of the present invention. Output waveform 1030 may be generated from a pulse width generator in microcomputer 22.

Figure 10E:
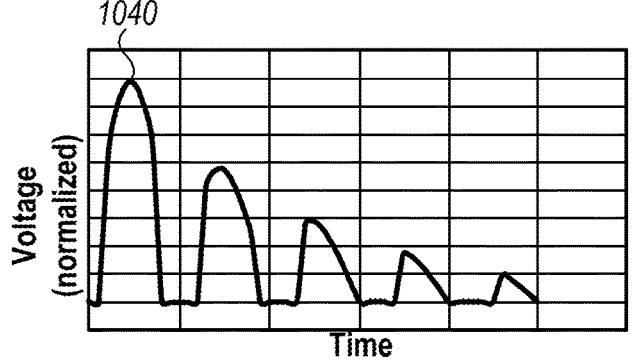
FIG. 10E is a defibrillation waveform, in accordance with some embodiments of the present invention.

FIG. 10E is a defibrillation waveform 1040, in accordance with some embodiments of the present invention.

Defibrillation signals applied to the subject are generated by applying the signals in FIG. 9E or 10E to a high frequency transformer (e.g., transformer 195). High voltage waveform 1040 may be used to generate a defibrillation signal where the cumulative energy delivered to the subject in the defibrillation signal may be critical.

When a defibrillation signal may be required to alleviate identified cardiac arrhythmia in portable pacing and defibrillation 10, transformers are used to step up the voltage waveform signals to high voltage levels as described previously. However, transformers may experience hysteresis losses that severely reduce the efficiency of the transformer. The hysteresis losses may result in the defibrillation voltage levels too low to be effective in alleviating the cardiac arrhythmia. Pre-magnetization may be used to minimize the hysteresis losses prior to generating the defibrillation signals. Pre-magnetization of the transformer core may allow for the application of multiple defibrillation signals to be applied to the subject if the previous defibrillation attempt failed.

In some embodiments of the present invention, the circuitry may be used to pre-magnetize the transformer core of the transformer. In some embodiments, pre-magnetizing the transformer core may include setting the remanence point of the transformer, also known as the retentivity point of the transformer so as to maximize the efficiency of the transformer. Depending on the magnetic material of the magnetic core of the transformer, the retentivity point may be set substantially close to the value of the flux density at saturation, which reduces the hysteresis loss of the transformer.

In some embodiments of the present invention, interface controller 105 may be configured to apply a series of current pulses to the primary coil of transformer 195 via IGBT drivers 255 and IGBT wave shaping unit 260 when relay 203 is positioned to couple the secondary coil of transformer 195 to dummy resistive load 200. The applied current pulses may move the retentivity point of the transformer substantially close to the value of the flux density of the transformer core where the transformer efficiency is maximized.

Figure 11:
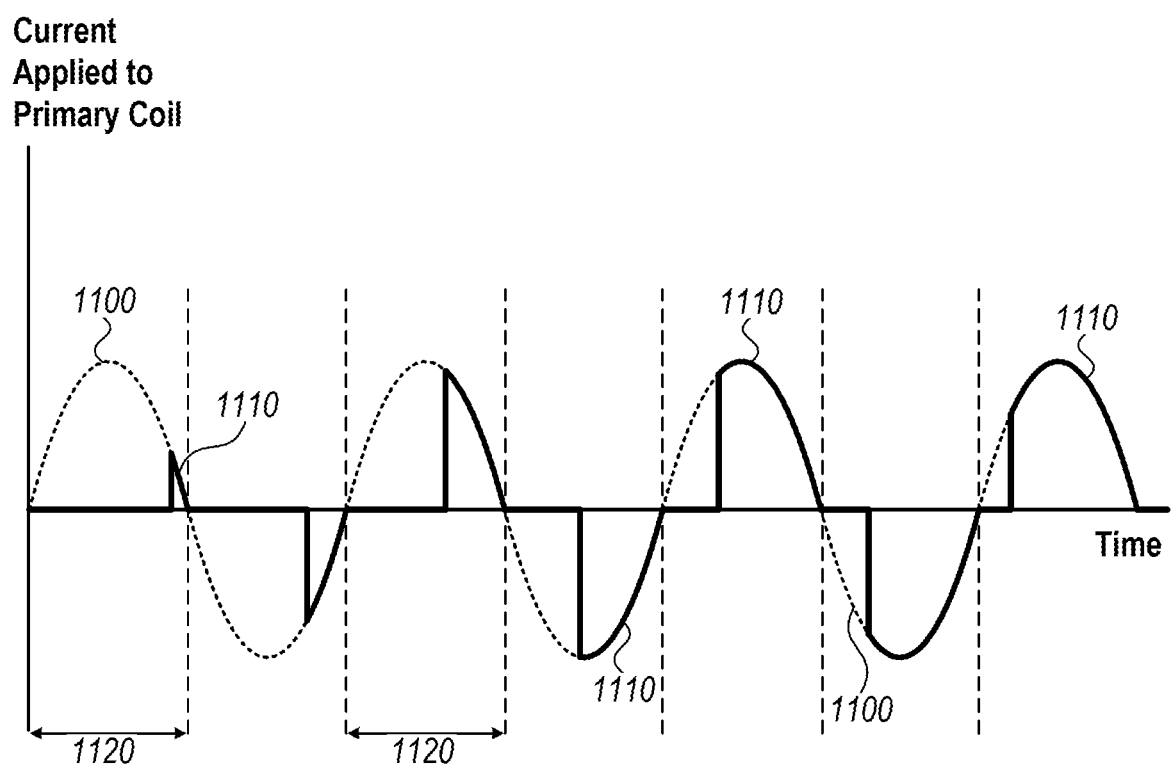
FIG. 11 is a graph illustrating a current waveform applied to the primary coil of a transformer for pre-magnetizing the transformer core, in accordance with some embodiments of the present invention.

FIG. 11 is a graph illustrating a current waveform 1110 applied to the primary coil of transformer 195 for pre-magnetizing the transformer core, in accordance with some embodiments of the present invention. Current waveform 1110 may generated in defibrillation subsystem 50 controlled by interface controller 105 in control unit 26. In some embodiments, current waveform 1110 includes a series of current pulses applied to the primary coil of transformer 195. Current waveform 1110 may be generated from a current signal 1100 derived from a mains electrical power source 14. The width of the current pulses is a fraction of the half cycle width of current signal 1100 where the fraction increases with each successive half cycle.

In some embodiments of the present invention, a system for cardiac pacing may include circuitry and at least two electrodes configured to be placed in contact with a chest of a subject. The circuitry is configured to receive electrocardiogram (ECG) signals from the at least two electrodes, to identify brachycardia or asystole or ventricular tachycardia in the subject based on the received ECG signals, upon identifying brachycardia or asystole or ventricular tachycardia, to shape a mains electrical source signal into a waveform applicable to a transformer for generating a pacing signal, to generate the pacing signal by applying the waveform to the transformer, and to apply the pacing signal through the at least two electrodes to the chest of the subject.

Figure 12:
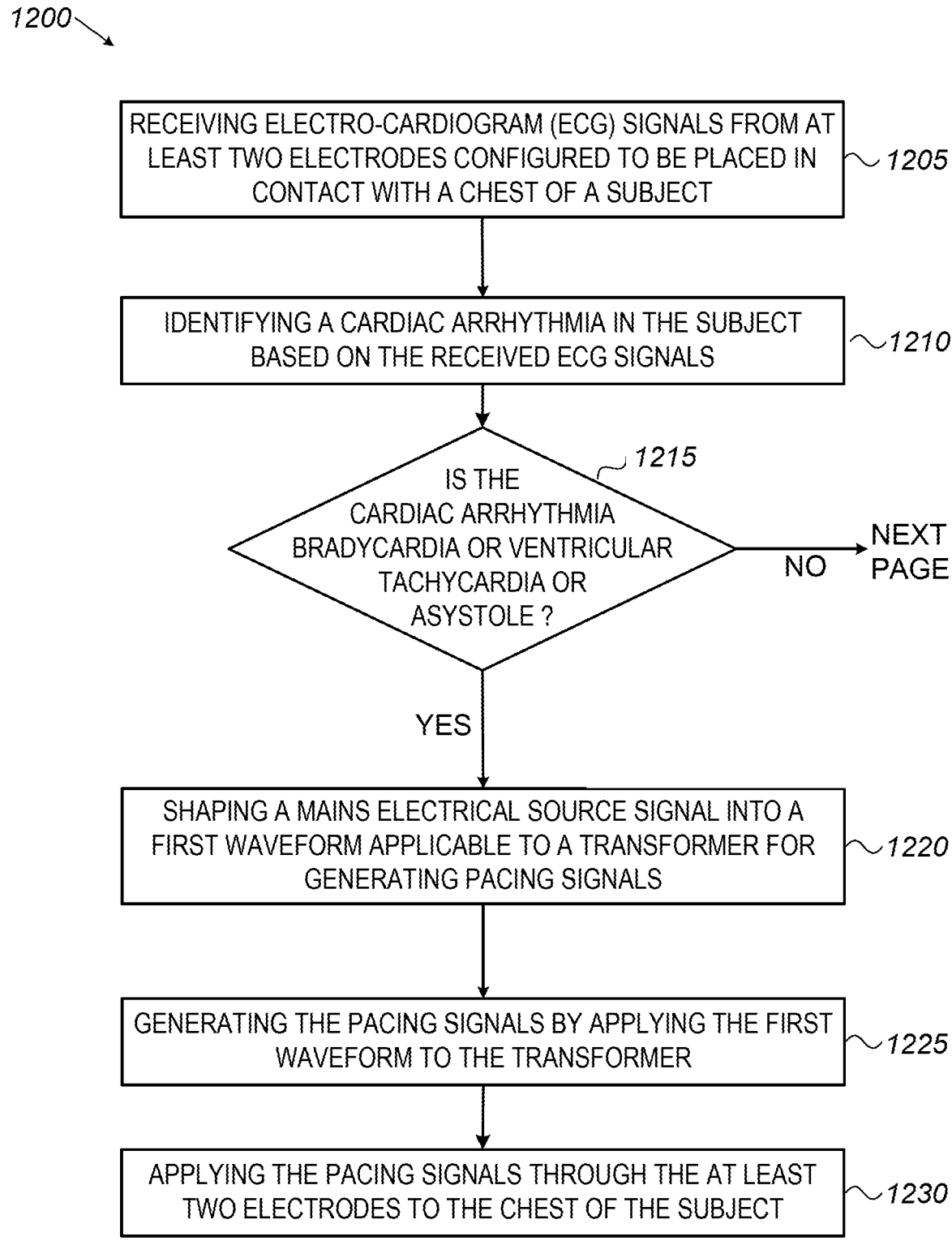
FIG. 12 is a flowchart depicting a method for cardiac pacing and defibrillation, in accordance with some embodiments of the present invention.
Figure 12:
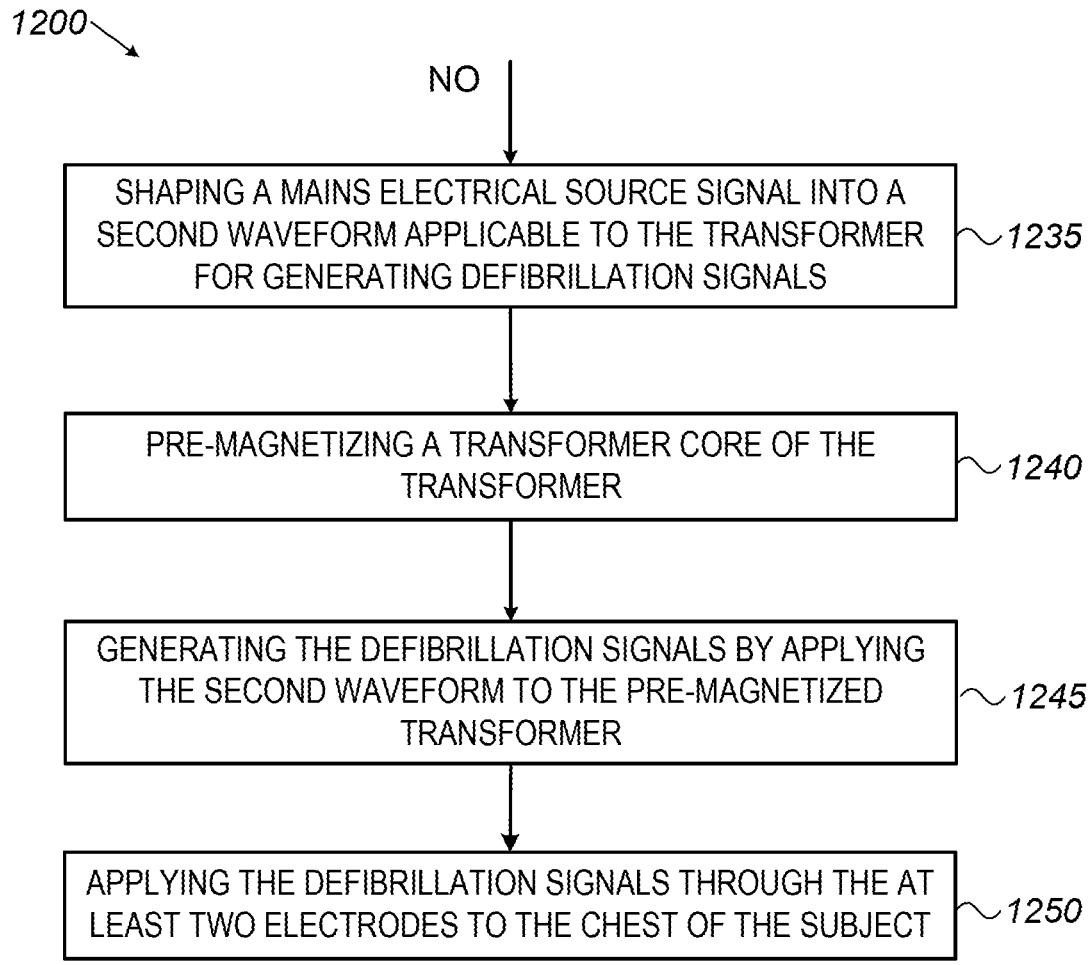

FIG. 12 is a flowchart depicting a method 1200 for cardiac pacing and defibrillation, in accordance with some embodiments of the present invention. In the example of FIG. 12, method 1200 may be executed by control unit 26 of cardiac pacing and defibrillation system 10.

Method 1200 may include receiving 1205 electro-cardiogram (ECG) signals from at least two electrodes (e.g., electrodes 46) configured to be placed in contact with a chest of a subject. Method 1200 may include identifying 1210 a cardiac arrhythmia in the subject based on the received ECG signals. Method 1200 may include a decision step 1215 to determine if the cardiac arrhythmia is bradycardia or asystole or ventricular tachycardia.

If yes in decision step 1215, the cardiac arrhythmia may include bradycardia or asystole or ventricular tachycardia. Method 1200 may include shaping 1220 a mains electrical source signal into a first waveform applicable to a transformer for generating pacing signals. Method 1200 may include generating 1225 the pacing signals by applying the first waveform to the transformer. Method 1200 may include applying 1230 the pacing signals through the at least two electrodes to the chest of the subject.

If no in decision step 1215, the cardiac arrhythmia may include ventricular fibrillation. Method 1200 may include shaping 1235 a mains electrical source signal into a second waveform applicable to the transformer for generating defibrillation signals. Method 1200 may include pre-magnetizing 1240 a transformer core of the transformer. Method 1200 may include generating 1245 the defibrillation signals by applying the second waveform to the pre-magnetized transformer. Method 1200 may include applying 1250 the defibrillation signals through the at least two electrodes to the chest of the subject.

It should be understood with respect to any flowchart referenced herein that the division of the illustrated method into discrete operations represented by blocks of the flowchart has been selected for convenience and clarity only. Alternative division of the illustrated method into discrete operations is possible with equivalent results. Such alternative division of the illustrated method into discrete operations should be understood as representing other embodiments of the illustrated method.

Similarly, it should be understood that, unless indicated otherwise, the illustrated order of execution of the operations represented by blocks of any flowchart referenced herein has been selected for convenience and clarity only. Operations of the illustrated method may be executed in an alternative order, or concurrently, with equivalent results. Such reordering of operations of the illustrated method should be understood as representing other embodiments of the illustrated method.

Different embodiments are disclosed herein. Features of certain embodiments may be combined with features of other embodiments; thus certain embodiments may be combinations of features of multiple embodiments. The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A method for cardiac pacing and defibrillation, the method comprising:
   in circuitry,
      receiving electro-cardiogram (ECG) signals from at least two electrodes configured to be placed in contact with a chest of a subject;
      identifying a cardiac arrhythmia in the subject based on the received ECG signals;
      selecting whether defibrillation signals or pacing signals are to be applied to the subject by setting the position of a selection relay;
      when the identified cardiac arrhythmia is bradycardia or asystole or ventricular tachycardia, shaping a mains electrical source signal into a first waveform applicable to a step-up transformer for generating pacing signals;
      generating the pacing signals by applying the first waveform to the step-up transformer; and
      applying the pacing signals through the at least two electrodes to the chest of the subject over long periods of time due to continuous connection to the mains electrical source; and
      when the identified cardiac arrhythmia is ventricular fibrillation,
      shaping the mains electrical source signal into a second waveform applicable to the step-up transformer for generating defibrillation signals;
      pre-magnetizing a transformer core of the step-up transformer to maximize energy transfer through the step-up transformer;
      generating the defibrillation signals by applying the second waveform to the pre-magnetized step-up transformer; and
      applying the defibrillation signals through the at least two electrodes to the chest of the subject over long periods of time due to continuous connection to the mains electrical source.

2. The method according to claim 1, wherein shaping the mains electrical source signal into the second waveform for generating the defibrillation signals comprises using a high frequency signal generator.

3. The method according to claim 1, wherein pre-magnetizing the step-up transformer core comprises applying a series of current pulses in a current waveform generated from the mains electrical power source signal to a primary coil of the step-up transformer.

4. The method according to claim 3, wherein pre-magnetizing the step-up transformer core comprises applying the series of current pulses to the primary coil when a secondary coil of the step-up transformer is coupled to a dummy resistive load.

5. The method according to claim 1, further comprising calling emergency medical services with a communication unit in the circuitry.

6. The method according to claim 1, further comprising audibly guiding a user of the system with an audio instruction and alarm unit in the circuitry.

7. The method according to claim 1, further comprising feeding a signal from the mains electrical source to a zero crossing detector and using an output of the zero crossing detector as a synchronization signal for the circuitry.

* * * * *